United States Patent
Schmitt et al.

(10) Patent No.: US 11,055,848 B2
(45) Date of Patent: Jul. 6, 2021

(54) DETERMINATION OF A FRACTIONAL FLOW RESERVE (FFR) VALUE FOR A STENOSIS OF A VESSEL

(71) Applicant: KONINKLIJKE PHILIPS N.V., Eindhoven (NL)

(72) Inventors: Holger Schmitt, Luetjensee (DE); Peter Forthmann, Sandesneben (DE); Michael Grass, Buchholz in der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1155 days.

(21) Appl. No.: 14/396,407

(22) PCT Filed: May 10, 2013

(86) PCT No.: PCT/IB2013/053801
§ 371 (c)(1),
(2) Date: Oct. 23, 2014

(87) PCT Pub. No.: WO2013/171644
PCT Pub. Date: Nov. 21, 2013

(65) Prior Publication Data
US 2015/0092999 A1    Apr. 2, 2015

Related U.S. Application Data

(60) Provisional application No. 61/646,525, filed on May 14, 2012.

(51) Int. Cl.
| | |
|---|---|
| *G06T 7/00* | (2017.01) |
| *A61B 6/00* | (2006.01) |
| *A61B 5/02* | (2006.01) |
| *A61B 5/00* | (2006.01) |
| *A61B 6/03* | (2006.01) |

(52) U.S. Cl.
CPC ........ *G06T 7/0014* (2013.01); *A61B 5/02007* (2013.01); *A61B 5/742* (2013.01); *A61B 6/032* (2013.01); *A61B 6/504* (2013.01); *A61B 6/5217* (2013.01); *G01N 2800/323* (2013.01); *G06T 2207/10088* (2013.01); *G06T 2207/10116* (2013.01); *G06T 2207/30104* (2013.01)

(58) Field of Classification Search
CPC ......... G06T 7/0014; G06T 2207/10088; G06T 2207/10116; G06T 2207/30104; A61B 6/504; A61B 5/02007; A61B 5/742; A61B 6/5217; A61B 6/032; G01N 2800/323; G16H 50/30
See application file for complete search history.

(56) References Cited

U.S. PATENT DOCUMENTS

| | | | |
|---|---|---|---|
| 8,157,742 B2 | 4/2012 | Taylor | |
| 8,200,466 B2 | 6/2012 | Spilker | |
| 8,249,815 B2 | 8/2012 | Taylor | |
| 8,315,812 B2 † | 11/2012 | Taylor | |
| 8,553,832 B2 * | 10/2013 | Camus | G16H 30/20 378/8 |
| 8,660,632 B2 | 2/2014 | Kobayashi | |
| 2010/0130878 A1 | 5/2010 | Lasso | |
| 2010/0241404 A1 | 9/2010 | Taylor | |
| 2011/0307231 A1 | 12/2011 | Kirchner | |
| 2012/0022843 A1 | 1/2012 | Ionasec | |
| 2012/0041318 A1 | 2/2012 | Taylor | |
| 2012/0041319 A1 | 2/2012 | Taylor | |
| 2012/0041320 A1 | 2/2012 | Taylor | |
| 2012/0041321 A1 | 2/2012 | Taylor | |
| 2012/0041322 A1 | 2/2012 | Taylor | |
| 2012/0041323 A1 | 2/2012 | Taylor | |
| 2012/0041324 A1 | 2/2012 | Taylor et al. | |
| 2012/0041735 A1 | 2/2012 | Taylor | |
| 2012/0041739 A1 | 2/2012 | Taylor | |
| 2012/0053919 A1 | 3/2012 | Taylor | |
| 2012/0053921 A1 | 3/2012 | Taylor | |

(Continued)

FOREIGN PATENT DOCUMENTS

| | | |
|---|---|---|
| CA | 2762123 A1 | 3/2010 |
| DE | 102008014792 | 6/2009 |

(Continued)

OTHER PUBLICATIONS

MATLAB (The Language of Technical Computing: Function Reference vol. 2:F-0, Version 7 (2004) by Mathworks Inc., Natick, MA:1-941.*
HeartFlow, Inc.; Corporate Website http//:heartflow.com/overview accessed Aug. 21, 2014.
Hud, Y., et al.; A validated predictive model of coronary fractional flow reserve; 2011; Journal of the Royal Society Interface; abstract, 1 page.

(Continued)

*Primary Examiner* — Lori A. Clow
(74) *Attorney, Agent, or Firm* — Larry Liberchuk

(57) ABSTRACT

A method includes determining at least one characteristic about a stenosis in a vessel of a patient from image data of the stenosis, mapping the characteristic to a predefined stenosis characteristic to fractional flow reserve value look up table, identifying the fractional flow reserve value in the look up table corresponding to the characteristic, and visually presenting the image data and the identified fractional flow reserve value. A system includes memory storing a pre-defined stenosis characteristic to fractional flow reserve value look up table, a metric determiner (118) that maps at least one characteristic about a stenosis in a vessel of a patient, which is determined from image data of the stenosis, to a characteristic in the look up table and identifies a fractional flow reserve value corresponding to the characteristic, and a display (116) that visually presents the image data and the identified fractional flow reserve value.

21 Claims, 3 Drawing Sheets

(56) References Cited

U.S. PATENT DOCUMENTS

| | | |
|---|---|---|
| 2012/0059246 A1 | 3/2012 | Taylor |
| 2012/0072190 A1 | 3/2012 | Sharma |
| 2012/0121151 A1 | 5/2012 | Bernhardt |
| 2012/0243761 A1 | 9/2012 | Senzig |

FOREIGN PATENT DOCUMENTS

| | | |
|---|---|---|
| JP | 2012021307 | 2/2012 |
| WO | 2004025572 | 3/2004 |
| WO | 200661814 | 6/2006 |
| WO | 200661815 | 6/2006 |
| WO | 201022762 | 3/2010 |

OTHER PUBLICATIONS

Kern, M. J., et al.; Physiological Assessment of Coronary Artery Disease in the Cardiac Catheterization Laboratory: A Scientific Statement From the American Heart Association Committee on Diagnostic and Interventional Cardiac Catheterization, Council on Clinical Cardiology; 2006; Circulation; 114:1321-1341.

Koo, B-K., et al.; Diagnosis of Ischemia-Causing Coronary Stenoses by Noninvasive Fractional Flow Reserve Computed From Coronary Computed Tomographic Angiograms; 2011; Journal of the American College of Cardiology; 58(19)1989-1997.

Kristensen, T. S., et al.; Correlation between coronary computed tomographic angiography and fractional flow reserve; 2010; International Journal of Cardiology; 144:200-205.

Pijls, N. H., et al.; Experimental basis of determining maximum coronary, myocardial, and collateral blood flow by pressure measurements for assessing functional stenosis severity before and after percutaneous transluminal coronary angioplasty; 1993; Circulation; 87:1354-1367.

Shalman, E., et al.; Evaluation of CFR and FFR Parameters by CFD Modeling of the Flow in a Stenosed Coronary Artery; 1999; Proc. of First Joint BMES/EMBS Conf. Serving Humanity, Advancing Technology; p. 217.

Tonino, P. A. L., et al.; Fractional Flow Reserve versus Angiography for Guiding Percutaneous Coronary Intervention; 2009; The New England Journal of Medicine; 360(3)213-224.

Tonino, et al., "Angiographic Versus Functional Severity of Coronary Artery Stenoses in the FAME Study Fractional Flow Reserve Versus Angiography in Multivessel Evaluation", Journal of the American College of Cardiology, vol. 55, No. 25, 2010, pp. 2816-2821.

\* cited by examiner
† cited by third party

US 11,055,848 B2

DETERMINATION OF A FRACTIONAL FLOW RESERVE (FFR) VALUE FOR A STENOSIS OF A VESSEL

CROSS REFERENCE TO RELATED APPLICATIONS

This application is a national filing of PCT application Ser. No. PCT/IB2013/053801, filed May 10, 2013, published as WO 2013/171644 A1 on Nov. 21, 2013, which claims the benefit of U.S. provisional application Ser. No. 61/646,525 filed May 14, 2012, which is incorporated herein by reference.

The following generally relates to determining a fractional flow reserve value for a stenosis in a vessel based on image data and a pre-defined stenosis characteristic to fractional flow reserve value look up table and is described with particular application to computed tomography (CT). However, the following is also amenable to other imaging modalities such as other modalities that produce three-dimensional (3D) angiography image data, including, but not limited to 3D rotational X-ray, 2D angiographic X-ray, magnetic resonance imaging (MRI), etc., and/or other imaging modalities.

A fractional flow reserve (FFR) value is a measurement of a pressure difference value across vessel stenosis, and the FFR value has been used to determine the likelihood that the stenosis impedes oxygen delivery to the heart muscle. Generally, an FFR value expresses the maximal flow down a vessel in the presence of a stenosis compared to the maximal flow in the hypothetical absence of the stenosis. The literature purports that the FFR value is based on an assumption that a pressure drop caused by a stenosis is indicative of a hemodynamic severity of the stenosis. As such, the FFR value is an important factor in the planning of percutaneous coronary interventions, e.g. stent placement.

Traditionally, an FFR value is measured invasively using a pressure wire to obtain the blood pressure before and after the stenosis. For a coronary FFR value, during coronary catheterization, a catheter is inserted into the femoral or radial arteries using a sheath and guide wire. A sensor affixed to the tip is positioned at the stenosis of interest, and the pressures are recorded across the stenosis during conditions promoted by various agents that effect vessel geometry, compliance and resistance, and/or other characteristics. The pressure value is an absolute number. The literature indicates that there is no absolute cut-off point at which FFR becomes abnormal; rather, there is a smooth transition, with a large grey zone of insecurity, with lower values indicating a more significant stenosis.

Unfortunately, the pressure wire used with this approach can be relatively expensive, and each invasive procedure poses a health risk to the patient. Approaches for non-invasive measurement of an FFR value also exist. Such approaches have included a patient specific computer simulation based on image data from a coronary CT angiography scan of the patient and geometric artery model derived from the image data. However, such simulations have been based on computational fluid dynamics (CFD) and are rather time-consuming. Currently, the cardiologist has to submit a CTA data set to an external institution and receives back the results hours later (e.g., 5 hours), which is cumbersome for the patient and the clinical workflow.

In view of the foregoing, there is an unresolved need for other approaches for determining a FFR value for a stenosis of a vessel.

Aspects described herein address the above-referenced problems and others.

In one aspect, a method includes determining at least one characteristic about a stenosis in a vessel of a patient from image data of the stenosis, mapping the at least one characteristic to a pre-defined stenosis characteristic to fractional flow reserve value look up table, identify the fractional flow reserve value in the look up table corresponding to the at least one characteristic, and visually presenting the image data and the identified fractional flow reserve value.

In another aspect, a system includes memory storing a pre-defined stenosis characteristic to fractional flow reserve value look up table. The system further includes a metric determiner that maps at least one characteristic about a stenosis in a vessel of a patient, which is determined from image data of the stenosis, to a characteristic in the look up table and identifies a fractional flow reserve value corresponding to the characteristic. The system further includes a display that visually presents the image data and the identified fractional flow reserve value.

In another aspect, a computer readable storage medium is encoded with computer readable instructions. The instructions, when executed by a processor, cause the processor to: determine a fractional flow reserve value for a patient based on a pre-defined stenosis characteristic to fractional flow reserve value look up table and at least one characteristic about a stenosis in a vessel of a patient, which is determined from image data of the stenosis.

The invention may take form in various components and arrangements of components, and in various steps and arrangements of steps. The drawings are only for purposes of illustrating the preferred embodiments and are not to be construed as limiting the invention.

FIG. 1 schematically illustrates an imaging system in connection with a metric determiner configured to at least determine an FFR value for a stenosis of a vessel of a patient.

Figure 1:
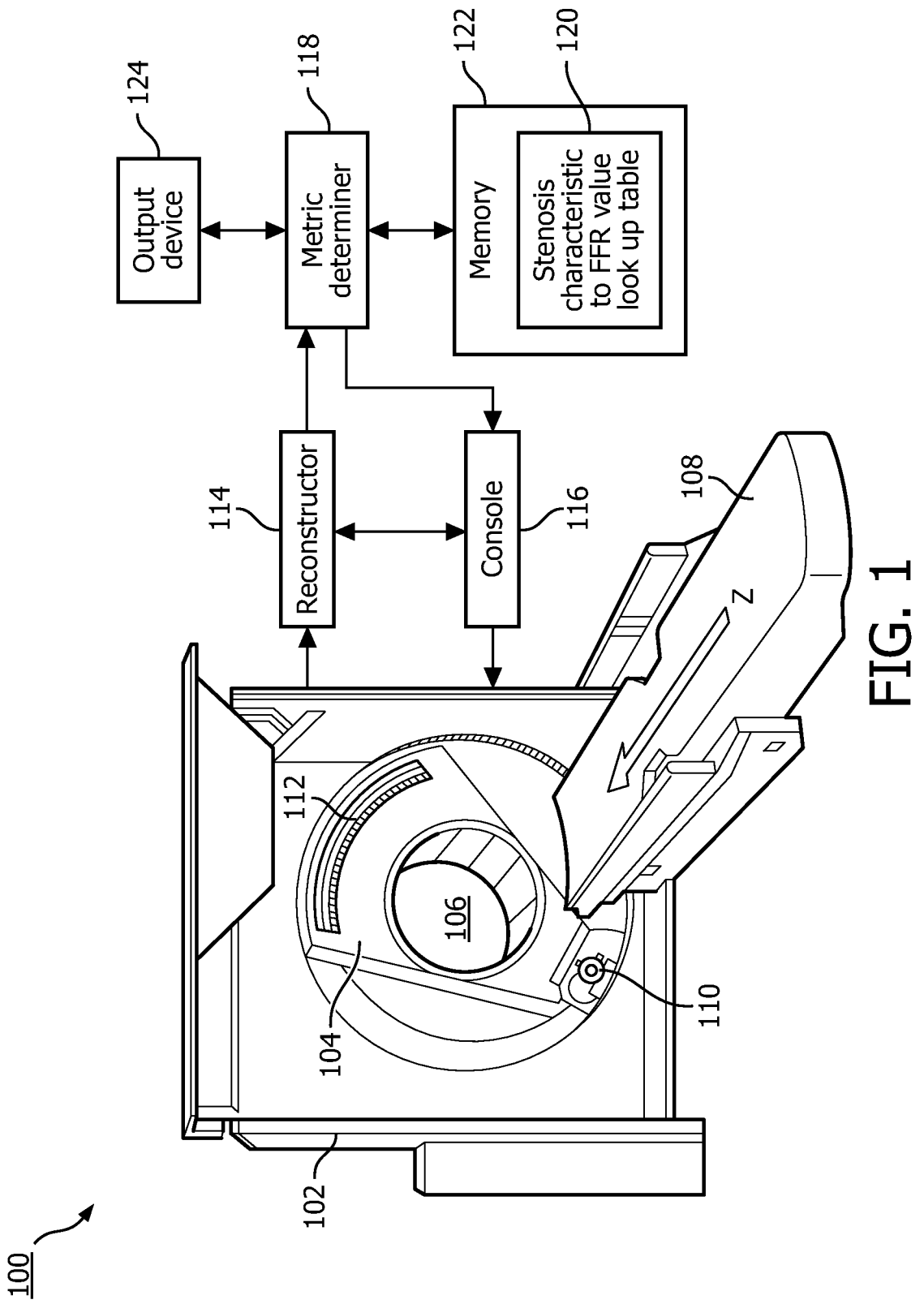

FIG. 1 schematically illustrates an imaging system 100 such as a CT scanner. The imaging system 100 includes a generally stationary gantry 102 and a rotating gantry 104, which is rotatably supported by the stationary gantry 102 and rotates around an examination region 106 about a z-axis. A subject support 108, such as a couch, supports an object or subject in the examination region 106.

A radiation source 110, such as an x-ray tube, is rotatably supported by the rotating gantry 104, rotates with the rotating gantry 104, and emits radiation that traverses the examination region 106. A radiation sensitive detector array 112 subtends an angular arc opposite the radiation source 110 across the examination region 106. The radiation sensitive detector array 112 detects radiation traversing the examination region 106 and generates a signal indicative thereof for each detected photon.

A reconstructor 114 reconstructs the projection, generating volumetric image data indicative of a scanned portion of a subject or object located in the imaging region 106. A general-purpose computing system or computer serves as an operator console 116. The console 116 includes a human readable output device such as a monitor and an input device such as a keyboard, mouse, etc. Software resident on the console 116 allows the operator to interact with and/or operate the scanner 100 via a graphical user interface (GUI) or otherwise.

A metric determiner 118 is configured to at least process image data representing vessels (e.g., coronary arteries, cerebral artery, etc.) and determine an FFR value for a stenosis at least one of the vessels. The metric determiner 118 may also determine one or more other metrics. The image data can be generated by the system 100, other CT imaging system, 3D rotational X-ray system, an MRI system, other imaging system that produce three-dimensional (3D) angiography image data, and/or other imaging system.

As described in greater detail below, in one non-limiting instance, the metric determiner 118 determines various stenosis characteristics from the image data and maps the characteristics values to an FFR value in a stenosis characteristic to FFR look up table 120 stored in memory 122, which may include a database, local and/or remote memory, and/or other form of data storage. The look up table 120, generally, can be pre-calculated, for example, once for all patients, a sub-group of particular patients, etc., using a synthetic software artery model(s) and includes a mapping for a pre-determined set of different length of stenosis and a pre-determined set of different diameters to FFR values. More than one look up table can be generated, and different look up tables may correspond to different types of patients.

Using the stenosis characteristic to FFR look up table 120, relative to sending CTA image data to an external institution for computational fluid dynamics (CFD), greatly reduces the effort to obtain an individual FFR value at least because instead of a full CFD simulation for each patient, only a smaller number geometric properties need to be determined and correlated to the look up table 120 to determine a FFR value. Examples of suitable characteristics for generating the look up table 120 and performing the determination include stenosis physical characteristics such as stenosis length, stenosis diameter, vessel curvature, distance of the stenosis to a branching point, etc., patient information such as blood pressure, patient age, vessel type, etc., and/or other information.

The metric determiner 118 can be implemented through at least one processor that executes at least one computer readable instruction stored in computer readable storage medium, such as physical memory or other non-transitory storage medium. The processor may also execute one or more computer readable instructions carried by a carrier wave, a signal or other transitory medium. The metric determiner 118, the memory 122, and/or the output device 124 may be part of a same apparatus (e.g., computing system) and/or different apparatuses. The illustrated metric determiner 118 can communicate with devices such as the console 116, output device 124 (e.g., a monitor, a filmer, portable memory, etc.), an input device (e.g., a keyboard, a mouse, etc.), and/or other device.

Figure 2:
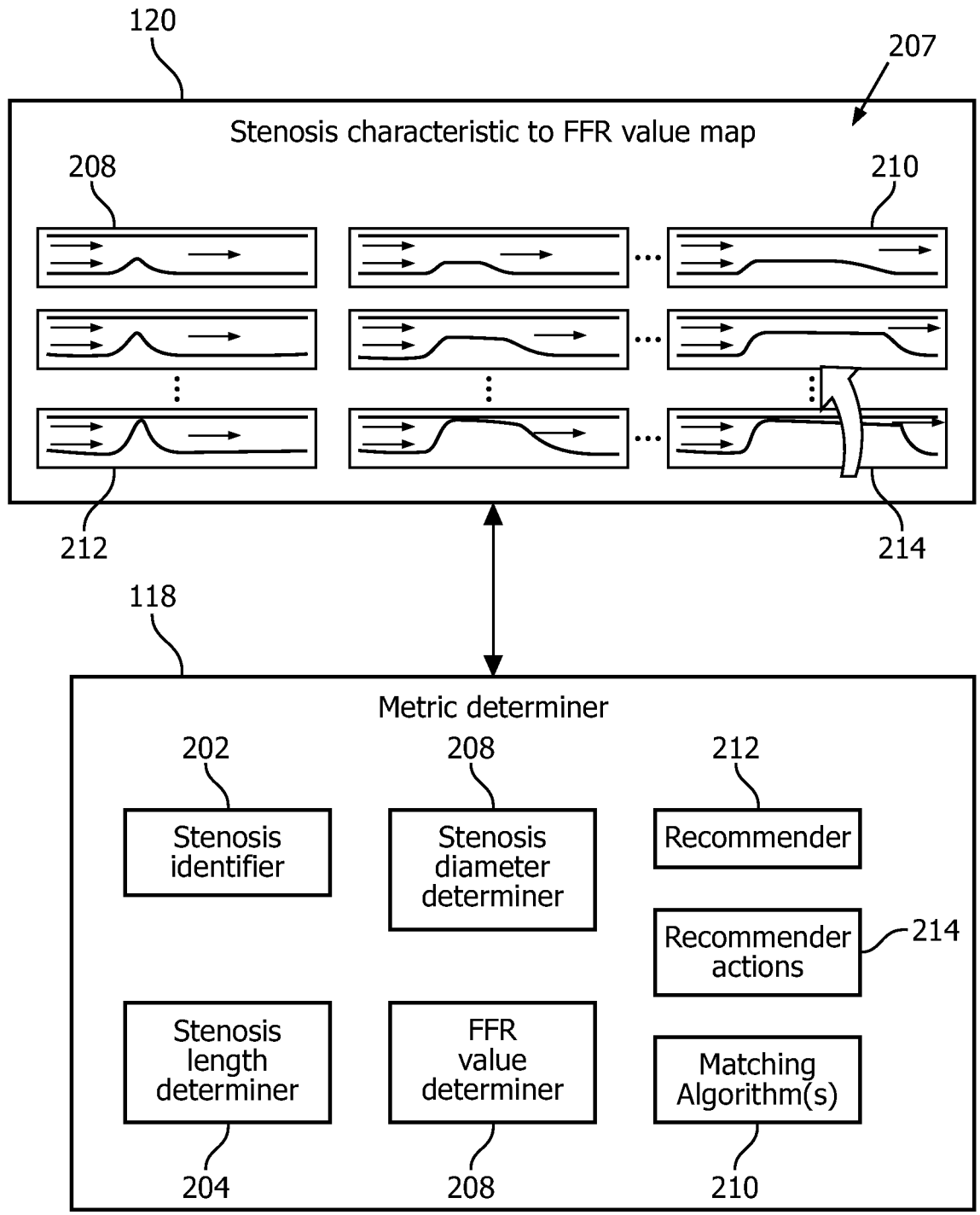
FIG. 2 illustrates an example of the metric determiner in connection with a pre-defined stenosis characteristic to fractional flow reserve value look up table.

FIG. 2 illustrates an example of the metric determiner 118 and the stenosis characteristic to FFR value look up table 120.

In this example, the metric determiner 118 includes a stenosis identifier 202. The stenosis identifier 202 identifies one or more stenoses in the image data. This can be achieved through automated approaches with authorized personal approval, manual approaches based on authorized personal input, or a combination of automatic and manual approaches.

The metric determiner 118 further includes a stenosis length determiner 204 that determines a length of one or more of the identified stenoses. Likewise, this can be achieved through automated approaches with authorized personal approval, manual approaches based on authorized personal input, or a combination of automatic and manual approaches.

The metric determiner 118 further includes a stenosis diameter determiner 206 that determines diameters along the length of one or more of the identified stenoses and identifies a minimum, average and/or other diameter Likewise, this can be achieved through automated approaches with authorized personal approval, manual approaches based on authorized personal input, or a combination of automatic and manual approaches.

Where 2D angiographic X-ray projections are available, one or more image based stenosis characteristic can be determined from a single or a multitude of 2D projections which are acquired under comparable imaging settings, such as, e.g. least foreshortening, maximum source detector distance, known angle, etc.

The metric determiner 118 further includes an FFR value determiner 208. In the illustrated embodiment, this includes mapping the determined length and minimum diameter of a stenosis to the stenosis characteristic to FFR value look up table 120 based on one or more matching algorithms 222. As shown, in this example, the stenosis characteristic to FFR value look up table 120 includes a 2D array of stenosis length and diameter entries 207, with entries with increasing length from entry 210 to entry 212 and decreasing diameter from the entry 212 to entry 214, and the greatest length and smallest diameter at entry 216. Other formats are also contemplated herein.

Each one of the entries 207 corresponds to a particular FFR value. The metric determiner 118 determines the closest or best match between the measured length and measured diameter and the length and diameter in the stenosis characteristic to FFR value look up table 120, and returns the corresponding FFR value as the FFR value for the stenosis in the image data. The value look up table 120 may or may not include the illustrated graphical representations, and can also return the corresponding graphical representation.

Where the measured length and/or the diameter do not match any particular entry 207, the matching algorithm(s) 222 can be employed. By way of example, in one instance, a matching algorithm may indicate that the metric determiner 118 should interpolate between neighboring entries to derive entries where the measured data does not match any look up table entry. Extrapolation and/or other techniques can be used to match the measured length and/or the diameter and determine an FFR value.

Where multiple entries 207 are equally likely (e.g., they are the same distance away from the measured stenosis diameter and length) or within a pre-determined range, a matching algorithm may instruct the metric determiner 118 to calculate an average FFR value from the individual FFR values. The average can be a straight or weighted average. In another instance, a matching algorithm may instruct the metric determiner 118 to select multiple FFR values as candidate FFR values.

In another instance, a matching algorithm may instruct the metric determiner 118 to select one of multiple FFR values based on a rule or priority, for example, which weights one of the measured stenosis characteristics greater than the other(s) stenosis characteristics. For example, where stenosis diameter and stenosis length correspond to multiple different FFR values, the algorithm may indicate that the stenosis diameter has priority over stenosis length, which may facilitate instructing the metric determiner 118 with selecting between the FFR values.

The literature indicates that the length of a stenosis and its minimum diameter are the strongest determinants of abnormal FFR. However, other information such as vessel curvature, distance of the stenosis to branching points, blood pressure, patient age, vessel type, etc. can be included in the stenosis characteristic to FFR value look up table 120 and/or used by the metric determiner 118 to determine a FFR value from the stenosis characteristic to FFR value look up table 120. Where further information is included the stenosis characteristic to FFR value look up table 120, the table becomes an N-dimensional look up table.

Optionally, the FFR value determiner 208 can additionally use the type of the vessel of interest to facilitate determining the FFR value. For example, where the coronary artery is of interest, the vessel of interest can be identified as the right coronary artery, the left coronary artery, the left circumflex artery, etc. Other vessels are also contemplated herein. This identification can be determined automatically and/or manually, for example, by metric determiner 118 and/or other component. The FFR value determiner 208 can then map the identified of vessel with the type of vessel in the stenosis characteristic to FFR value look up table 120, and use this information in addition or in alternative to the information discussed herein to determine an FFR value.

The metric determiner 118 at least one of visually presents the FFR value and/or conveys the FFR value to another device. By way of example, in one instance, the metric determiner 118 visually presents the image data showing the stenosis and the FFR value via a monitor output device 124. In another instance, the metric determiner 118 conveys the FFR value to the console 116, which visually presents the image data showing the stenosis and the FFR value.

In another instance, the graphical representation shown in FIG. 2 for a corresponding entry 207 is displayed in alternative or addition to the FFR value. In another instance, a color overlay in which each color represents a known degree of stenosis is displayed in alternative or addition to the FFR value and/or the graphical representation. In another embodiment, this information can be sent to a filmer, a printer, another computer, further processed, etc.

An optional recommender 218 recommends a course of action based on the FFR value and/or other information such as clinical information about the patient, patient history, other information derived from the image data, etc. In the illustrated embodiment, the recommender 218 recommends the course of action based on a set of pre-defined recommended actions 220. The optional recommender 218 generates a signal indicative of the recommended course of action, and conveys the signal to the console 116, the output device 124 and/or other apparatus.

It is to be appreciated that the stenosis characteristic to FFR value look up table 120 may be stored in formats other than a look up table.

Figure 3:
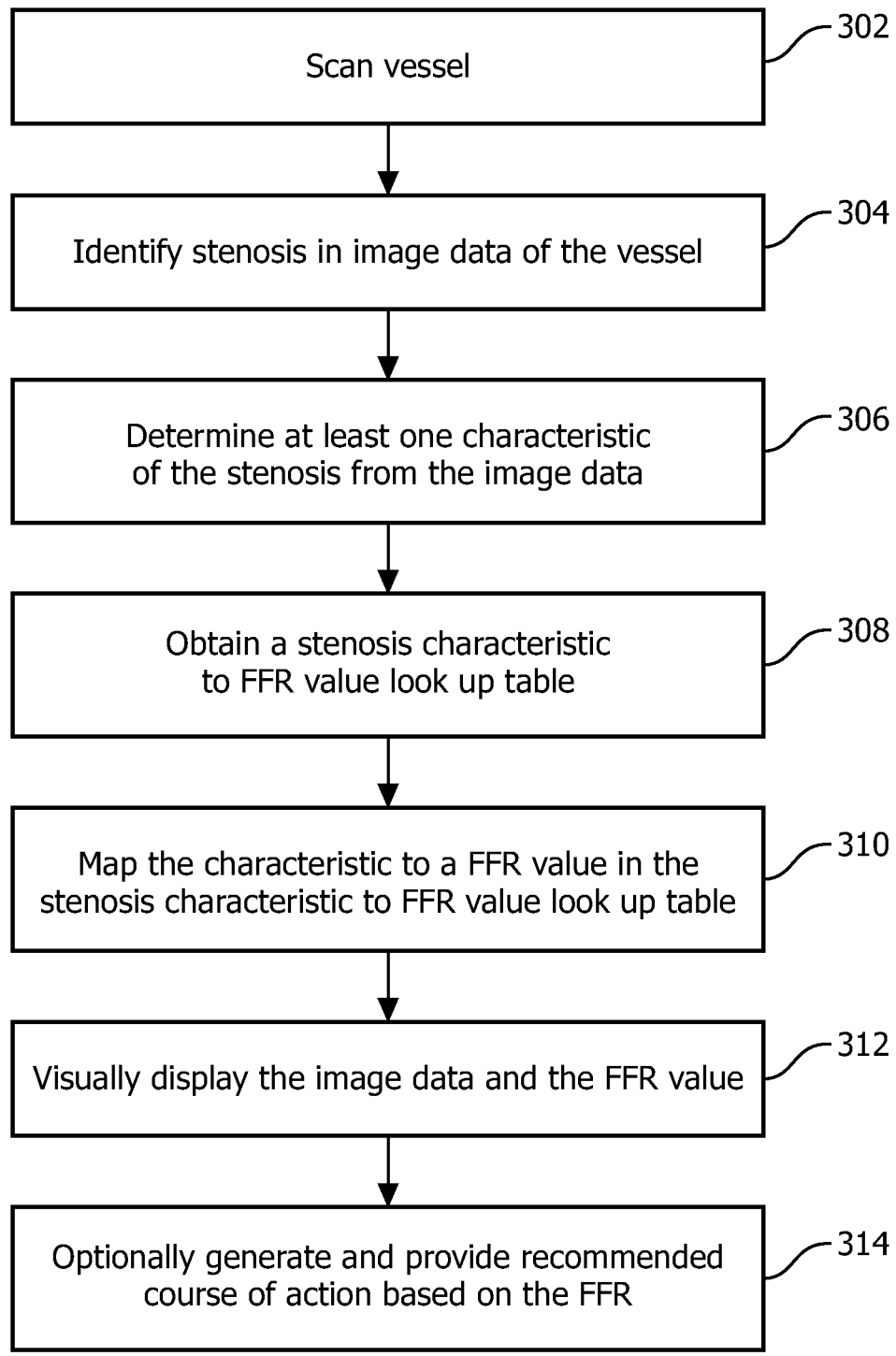
FIG. 3 illustrates an example method for determining an FFR value for a stenosis of a vessel of a patient.

FIG. 3 illustrates an example method for determining an FFR value for a stenosis in a vessel of a patient based on characteristics of the stenosis determined from image data and a stenosis characteristic to FFR value look up table 120.

It is to be appreciated that the ordering of the acts is not limiting. As such, other orderings are contemplated herein. In addition, one or more acts may be omitted and/or one or more additional acts may be included.

At 302, a scan of a vessel is performed.

At 304, a stenosis of the vessel is identified.

At 306, at least one characteristic of the identified stenosis is determined based on the image data. Examples of characteristics include, but are not limited to, stenosis length, stenosis diameter, vessel curvature, distance of the stenosis to a branching points, vessel type, and/or other characteristics.

At 308, a pre-calculated stenosis characteristic to FFR value look up table is obtained. An example of a suitable stenosis characteristic to FFR value look up table is the stenosis characteristic to FFR value look up table 120 discussed herein.

At 310, the at least one characteristic is mapped to an FFR value in the pre-calculated stenosis characteristic to FFR value look up table.

At 312, at least the FFR value is visually presented along with the image data. As discussed, other information such as the entry in the map, color coding, etc. can be displayed.

At 314, optionally, a recommended course of action is generated and provided based on the FFR value.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A computer-implemented medical imaging method in order to improve a clinical workflow and shorten treatment planning time, the method comprising:
   storing in a memory a look up table, wherein, in the look up table, each functional flow reserve (FFR) value of a plurality of FFR values corresponds to at least one of a predetermined stenosis length and a predetermined stenosis diameter;
   emitting, by a medical imaging system, radiation that traverses an examination region;
   scanning, by the medical imaging system, a vessel of a patient in the examination region;
   detecting the radiation that traverses the examination region, to generate vessel image data of a stenosis;
   transmitting to a display one FFR value of the plurality of FFR values in the stored look up table, wherein the transmitted FFR value corresponds to at least one of a stenosis length from the vessel image data; and a stenosis diameter from the vessel image data; and
   displaying the vessel image data and the transmitted FFR value on the display.

2. The method of claim 1, wherein the stenosis diameter from the vessel image is one of:
   a minimum diameter along a longitudinal direction of the stenosis; and
   an average diameter along the the longitudinal direction of the stenosis.

3. The method of claim 1, wherein the transmitted FFR value further corresponds to at least one of:
   a vessel curvature;
   a distance of the stenosis to a branching point; and
   a vessel type.

4. The method of claim 1, wherein the transmitted FFR value further corresponds to information about the patient.

5. The method of claim 4, wherein the information includes at least one of:
 a blood pressure of the patient; and
 an age of the patient.

6. The method of claim 1, wherein the look up table includes a precalculated look up table for all or a sub-group of patients.

7. The method of claim 1, wherein the look up table includes an N-dimensional array of entries.

8. The method of claim 1, wherein when the at least one of the stenosis length from the vessel image data and the stenosis diameter from the vessel image data does not directly match any of a plurality of entries in the look up table, the transmitted FFR value is an interposed FFR value between FFR values that cvorrespond to neighboring entries of the plurality of entries.

9. The method of claim 1, wherein when the at least one of the stenosis length from the vessel image data and the stenosis diameter from the vessel image data does not directly match any of a plurality of entries in the look up table, the transmitted FFR value is an FFR value that corresponds to a closest entry among the plurality of entries.

10. The method of claim 1, wherein when the at least one of the stenosis length from the vessel image data and the stenosis diameter from the vessel image data does not directly match any of a plurality of entries in the look up table, the transmitted FFR value is an average FFR value of FFr values that correspond to neighboring entries of the plurality of entries.

11. The method of claim 1, further comprising:
 displaying a color overlay over the vessel image data, wherein the color overlay indicates a severity of the stenosis.

12. The method of claim 1, further comprising:
 displaying a recommended course of action corresponding to the transmitted FFR value.

13. A computer-implemented medical imaging system in order to improve a clinical workflow and shorten treatment planning time, the system comprising:
 a memory that stores a plurality of instructions and stores a look up table, wherein, in the look up table, each fractional flow reserve (FFR) value of a plurality of FFR values corresponds to at least one of a predetermined stenosis length and a predetermined stenosis diameter;
 a radiation source configured to:
  emit radiation that traverses an examination region; and
  scan a vessel of a patient in the examination region;
 a radiation sensitive detector configured to detect the radiation that traverses the examination region such that vessel image data of a stenosis is generated;
 processor circuitry that couples to the memory and that is configured to execute the plurality of instructions to transmit one FFR value of the plurality of FFR values in the stored look up table, wherein the transmitted FFR value corresponds to at least one of a stenosis length from the vessel image data; and a stenosis diameter from the vessel image data; and
 a display configured to display the vessel image data and the transmitted FFR value.

14. The system of claim 13, wherein the transmitted FFR further corresponds to at least one of:
 a vessel curvature;
 a distance of the stenosis to a branching point; and
 a vessel type.

15. The system of claim 13, wherein the transmitted FFR value further corresponds to at least one characteristic about the patient.

16. The system claim 13, wherein the look up table includes a precalculated look up table for all or a sub-group of patients.

17. The system of claim 13, wherein when the at least one of the stenosis length from the vessel image data and the stenosis diameter from the vessel image data does not directly match any of a plurality of entries in the look up table, the transmitted FFR value is an interposed FFR value between FFR values that correspond to neighboring entries of the plurality of entries.

18. The system of claim 13, wherein when the at least one of the stenosis length from the vessel image data and the stenosis diameter from the vessel image data does not directly match any of a plurality of entries in the look up table, the transmitted FFR value is an FFR value that corresponds to a closest entry among the plurality of entries.

19. The system of claim 13, wherein when the at least one of the stenosis length from the vessel image data and the stenosis diameter from the vessel image data does not directly match any of a plurality of entries in the look up table, the transmitted FFR value is an average FFR value of FFR values that correspond to neighboring entries of the plurality of entries.

20. The system of claim 13, wherein the vessel image data is displayed with a color overlay that indicates a severity of the stenosis.

21. The system of claim 13, wherein the display is configured to display a recommended course of action corresponding to the transmitted FFR value.

* * * * *